United States Patent
Wahl et al.

(10) Patent No.: US 11,350,924 B2
(45) Date of Patent: Jun. 7, 2022

(54) KNOTLESS SUTURE ANCHOR

(71) Applicant: In2Bones USA, LLC, Memphis, TN (US)

(72) Inventors: Rebecca Hawkins Wahl, Escondido, CA (US); Arley Perez, Memphis, TN (US)

(73) Assignee: In2Bones USA, LLC, Memphis, TN (US)

( * ) Notice: Subject to any disclaimer, the term of this patent is extended or adjusted under 35 U.S.C. 154(b) by 109 days.

(21) Appl. No.: 16/424,276

(22) Filed: May 28, 2019

(65) Prior Publication Data

US 2019/0365369 A1 Dec. 5, 2019

Related U.S. Application Data

(60) Provisional application No. 62/677,889, filed on May 30, 2018.

(51) Int. Cl.
*A61B 17/04* (2006.01)

(52) U.S. Cl.
CPC .. *A61B 17/0401* (2013.01); *A61B 2017/0414* (2013.01); *A61B 2017/0427* (2013.01)

(58) Field of Classification Search
CPC ........ A61B 17/0401; A61B 2017/0427; A61B 2017/0414; A61B 90/40; A61B 2090/0807; A61B 2017/0438; A61B 2017/0412

See application file for complete search history.

(56) References Cited

U.S. PATENT DOCUMENTS

| | | | |
|---|---|---|---|
| 2003/0065331 A1* | 4/2003 | Donnelly | A61B 17/0401 606/232 |
| 2009/0234387 A1* | 9/2009 | Miller | A61B 17/0401 606/232 |
| 2010/0063542 A1 | 3/2010 | Van Der Burg et al. | |
| 2013/0035721 A1* | 2/2013 | Brunelle | A61F 2/0811 606/232 |
| 2013/0158599 A1* | 6/2013 | Hester | A61B 17/0401 606/232 |
| 2013/0267998 A1* | 10/2013 | Vijay | A61B 17/0401 606/232 |
| 2014/0081323 A1* | 3/2014 | Hawkins | A61B 17/0401 606/232 |
| 2014/0207189 A1 | 7/2014 | Foerster et al. | |
| 2015/0201923 A1 | 7/2015 | Fan et al. | |
| 2018/0000476 A1* | 1/2018 | Spenciner | A61B 17/0401 |

* cited by examiner

*Primary Examiner* — Wade Miles
*Assistant Examiner* — Mikail A Mannan
(74) *Attorney, Agent, or Firm* — Rutan & Tucker LLP; Hani Z. Sayed

(57) ABSTRACT

An apparatus and methods are provided for a suture anchor to fixate sutures and tissue to bone. The suture anchor comprises an elongate member to be inserted into a bone hole. Barbs along the length of the elongate member engage with an inner wall of the bone hole. An eyelet in a distal aspect of the elongate member is configured to receive a suture. First and second channels extend helically along opposite sides of the elongate member. The eyelet includes first and second openings on opposite sides of the distal aspect. The first opening and the first channel enable applying tension to the suture after implantation into the bone hole. The second opening enables placing the suture into a final position along the barbs after implantation into the bone hole. A proximal aspect of the elongate member receives an instrument for implanting the suture anchor into the bone hole.

21 Claims, 2 Drawing Sheets

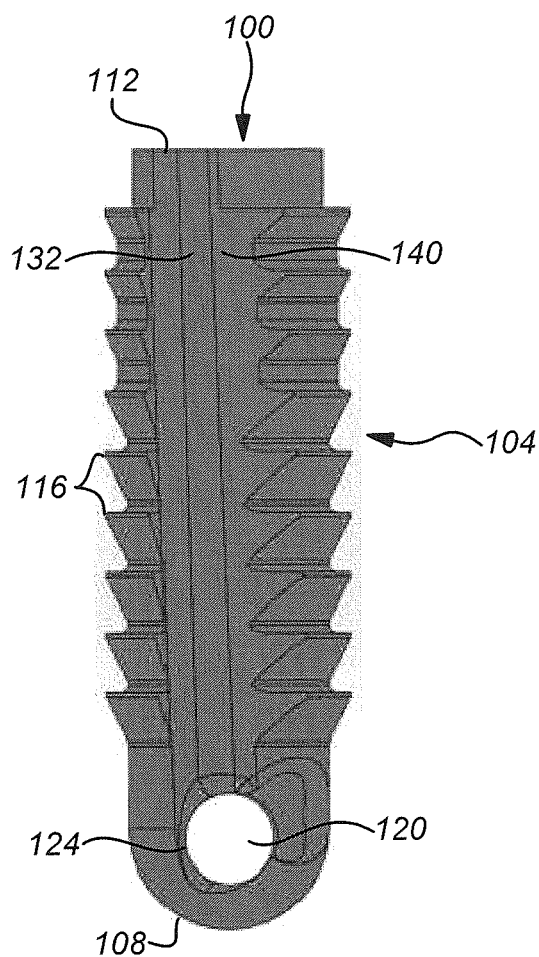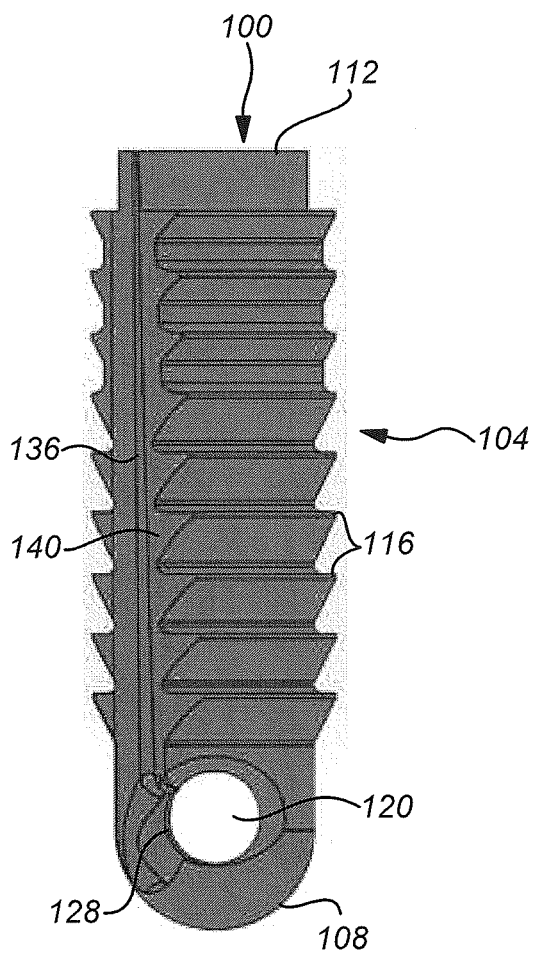
FIG. 1   FIG. 2
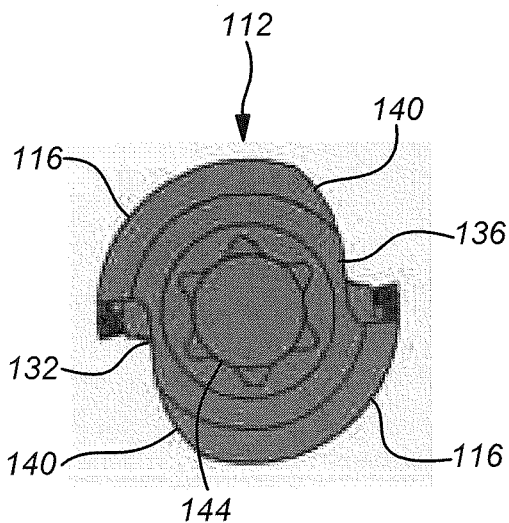
FIG. 3

KNOTLESS SUTURE ANCHOR

PRIORITY

This application claims the benefit of and priority to U.S. Provisional Application, entitled "Knotless Suture Anchor," filed on May 30, 2018 and having application Ser. No. 62/677,889, the entirety of said application being incorporated herein by reference.

FIELD

Embodiments of the present disclosure generally relate to the field of fixating tissue to bone. More specifically, embodiments of the disclosure relate to devices and methods for fixating sutures and tissues to bone.

BACKGROUND

When soft tissue, such as a ligament or a tendon, becomes detached from a bone, surgery is usually required to reattach the soft tissue to the bone. In some instances, a soft tissue graft may be attached to the bone to encourage regrowth and permanent attachment. The soft tissue may be reattached to the bone by way of any of various fixation devices, such as sutures, screws, staples, wedges, plugs, and the like. For example, a soft tissue graft may be fixated to a bone by driving a screw into a drilled bone hole and trapping an end of the graft between the screw and the bone hole. In another typical example, the soft tissue graft may be pinned against the bone by way of staples, or by way of sutures tied around an end of the graft.

Moreover, in many instances threaded suture anchors may be used to reattach soft tissue to bone. In many applications, however, various suture knots must be tied to couple the suture to the suture anchors, or to secure the soft tissue to the bone. As will be appreciated, tying one or more suture knots during surgery tends to be tedious and time-consuming. As such, there is a continuing desire to develop improved devices for fixating sutures and soft tissue to bone.

SUMMARY

An apparatus and a method are provided for a suture anchor configured to fixate sutures and soft tissue to bone. The suture anchor comprises an elongate member configured to be inserted into a drilled bone hole. A plurality of barbs are disposed along the length of the elongate member. The barbs are configured to engage with an inner wall of the bone hole upon turning of the suture anchor through a predetermined angle. An eyelet disposed in a distal aspect of the elongate member is configured to receive a suture. A first channel and a second channel extend helically along opposite sides of the elongate member. The eyelet includes a first opening and a second opening disposed on opposite sides of the distal aspect. The first opening is oriented with respect to the first channel to enable dynamic tensioning of the suture after the suture anchor has been inserted into the bone hole. The second opening is configured to enable placing the suture into a final position with respect to the barbs after implantation of the suture anchor into the bone hole. A proximal aspect of the elongate member is configured to receive an instrument for implanting the suture anchor into the bone hole.

In an exemplary embodiment, a suture anchor comprises: an elongate member configured to be inserted into a drilled bone hole; a plurality of barbs disposed along the length of the elongate member; an eyelet disposed in a distal aspect of the elongate member and configured to receive a suture; a first channel and a second channel extending along opposite sides of the elongate member; and a proximal aspect of the elongate member configured to receive an instrument for implanting the suture anchor into the bone hole.

In another exemplary embodiment, the proximal aspect includes a shaped hole configured to receive the instrument. In another exemplary embodiment, the elongate member is comprised of a suitable thermoplastic polymer material. In another exemplary embodiment, the suitable thermoplastic polymer material includes polyether ether ketone (PEEK).

In another exemplary embodiment, the eyelet is configured to receive a suture passed therethrough by way of a suture passer. In another exemplary embodiment, the eyelet includes a first opening and a second opening disposed on opposite sides of the distal aspect. In another exemplary embodiment, the first opening is oriented with respect to the first channel so as to enable applying tension to the suture after the suture anchor has been inserted into the bone hole. In another exemplary embodiment, the second opening is configured to enable placing the suture into a final position with respect to the plurality of barbs after implantation of the suture anchor into the bone hole. In another exemplary embodiment, the second opening is proximal of the first opening and canted to facilitate the final position of the suture.

In another exemplary embodiment, the first channel and the second channel are disposed with respect to the eyelet so as to enable applying tension to the suture after the suture anchor has been inserted into the bone hole. In another exemplary embodiment, one or more of the first channel and the second channel are helically disposed along the elongate member so as to graduate compression of the suture between the plurality of barbs and an inner wall of the bone hole during rotation of the elongate member within the bone hole. In another exemplary embodiment, the eyelet and the plurality of barbs cooperate to cause the suture to remain compressed between the plurality of barbs and the bone hole after rotation of the elongate member. In another exemplary embodiment, the plurality of barbs are configured to engage with an inner wall of the bone hole upon turning of the suture anchor through a predetermined angle. In another exemplary embodiment, the predetermined angle comprises an angle of substantially 90-degrees clockwise with respect to the proximal aspect.

In another exemplary embodiment, a depth line is disposed on the elongate member to indicate a proximal end of the first channel and the second channel. In another exemplary embodiment, the depth line indicates a depth within the bone hole to which the elongate member may be inserted that allows for final tensioning of the suture.

In an exemplary embodiment, a method for a suture anchor comprises: forming an elongate member comprising a suitable thermoplastic polymer material; arranging a plurality of barbs along a length of the elongate member; disposing an eyelet in a distal aspect of the elongate member; configuring the eyelet to receive a suture; extending a first channel and a second channel along opposite sides of the elongate member; and shaping a proximal aspect of the elongate member to receive an instrument for implanting the suture anchor into the bone hole.

In another exemplary embodiment, configuring the eyelet includes orienting a first opening of the eyelet with respect to the first channel so as to enable applying tension to the suture after the suture anchor has been inserted into the bone hole. In another exemplary embodiment, configuring the eyelet includes configuring a second opening of the eyelet to enable placing the suture into a final position with respect to the plurality of barbs after implantation of the suture anchor into the bone hole.

In another exemplary embodiment, extending the first channel and the second channel includes helically disposing one or more of the first and second channels along the elongate member, such that the suture becomes gradually compressed between the plurality of barbs and the bone hole during rotation of the elongate member within the bone hole. In another exemplary embodiment, arranging includes configuring the plurality of barbs to cooperate with the eyelet to cause the suture to remain compressed between the plurality of barbs and the bone hole after rotation of the elongate member. In another exemplary embodiment, arranging further includes configuring the plurality of barbs to engage with a wall of the bone hole upon turning of the suture anchor through a predetermined angle. In another exemplary embodiment, shaping includes disposing a depth line on the elongate member to indicate a proximal end of the first channel and the second channel, such that the depth line indicates a depth within the bone hole to which the elongate member may be inserted that allows for final tensioning of the suture.

BRIEF DESCRIPTION OF THE DRAWINGS

The drawings refer to embodiments of the present disclosure in which:

FIG. 1 illustrates a first side plan view of an exemplary embodiment of a suture anchor for fixating sutures and soft tissue to bone;

FIG. 2 illustrates a second side plan view of the suture anchor of FIG. 1;

FIG. 3 illustrates a top plan view of a proximal aspect of the suture anchor of FIG. 1;

Figure 4:
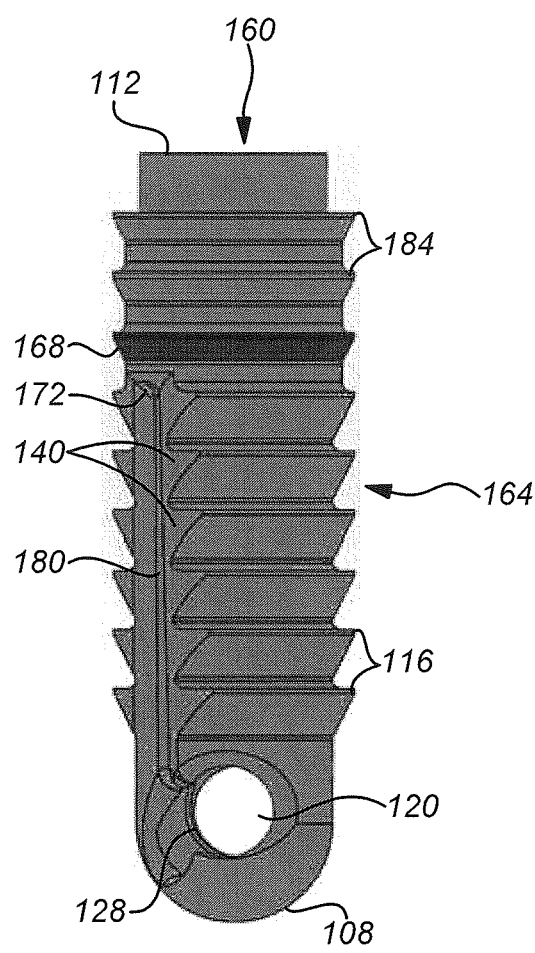
FIG. 4 illustrates a first side plan view of an exemplary embodiment of a suture anchor for fixating sutures and soft tissue to bone.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first suture," may be made. However, the specific numeric reference should not be interpreted as a literal sequential order but rather interpreted that the "first suture" is different than a "second suture." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

When soft tissue, such as a ligament or a tendon, becomes detached from a bone, surgery is usually required to reattach the soft tissue to the bone. Although threaded suture anchors may be used to reattach soft tissue to bone, in many applications various suture knots must be tied to couple the suture to the suture anchors, or to secure the soft tissue to the bone. Tying one or more suture knots during surgery generally tends to be tedious and time-consuming. As such, there is a continuing need for improved devices for fixating sutures and soft tissue to bone. Embodiments presented herein provide suture anchors configured to fixate sutures and soft tissue to bone.

FIGS. 1-3 illustrate an exemplary embodiment of a suture anchor 100 for fixating sutures and soft tissues to bone. The suture anchor 100 comprises a generally elongate member 104 configured to be inserted into a drilled bone hole. The elongate member 104 includes a distal aspect 108 configured to retain a suture, and a proximal aspect 112 configured to receive a suitable instrument for implanting the suture anchor 100 into the bone hole. The elongate member 104 may be comprised of any rigid biocompatible material, such as any of various suitable thermoplastic polymer materials. In one embodiment, for example, the elongate member 104 is comprised of polyether ether ketone (PEEK).

A plurality of barbs 116 disposed along the length of the elongate member 104 are configured to engage with an inner wall of the bone hole, such that the suture anchor 100 remains fixated therein. Once the suture anchor 100 is inserted into the bone hole and actuated, as described herein, the suture is fixated to the bone and available to be coupled with soft tissue that is to be attached to the bone. As will be appreciated, the suture anchor 100 enables a surgeon to fixate the suture to the bone without having to tie knots in the suture.

As best shown in FIGS. 1-2, an eyelet 120 is disposed in the distal aspect 108 and configured to receive a strand of suture or a leg of a loop of suture. The eyelet 120 includes a first opening 124 on one side of the elongate member 104 and a second opening 128 on an opposite side of the elongate member 104. As such, the eyelet 120 is oriented generally perpendicular to a longitudinal axis of the elongate member 104. In some embodiments, the first opening 124 may be positioned slightly distal of the second opening 128 as is found to be beneficial. It is contemplated that in practice, the strand of suture or the leg of a loop of suture may be drawn through the eyelet 120 by way of a suture passer.

As shown in FIG. 1, the first opening 124 is aligned with a first channel 132 that extends helically along the length of the elongate member 104. It is contemplated that the suture may remain in the first channel 132 while the suture anchor 100 is inserted into the drilled bone hole. The relationship between the first opening 124 and the first channel 132, illustrated in FIG. 1, enables a practitioner, such as a surgeon to apply tension to the suture after the suture anchor 100 has been inserted into the bone hole.

As best shown in FIG. 2, the second opening 128 is adjacent to distal end of a second channel 136 that extends helically along the length of the elongate member 104, similarly to the first channel 132. In the illustrated embodiment of FIGS. 1-3, the first and second channels 132, 136 extend along opposite sides of the elongate member 104. It is contemplated that the suture anchor 100 is not to be limited to two channels, such as channels 132, 136, extending along opposite sides of the elongate member 104. For example, in some embodiments, three or more channels may be disposed uniformly around the circumference of the elongate member 104 and extended helically along the length of the elongate member 104. As such, it should be understood that more or less than two channels may be implemented along other than opposite sides of the elongate member 104, without limitation.

With continuing reference to FIG. 2, the second opening 128 is oriented with respect to the second channel 136 so as to enable placing the suture into a final position between the plurality of barbs 116 and an interior wall of the drilled bone hole after implantation of the suture anchor 100 into the bone hole. More specifically, once the suture anchor 100 is inserted into the bone hole and the suture has been desirably tensioned by way of the first channel 132, as described herein, the suture anchor 100 may be actuated by rotating the suture anchor through a predefined angle to migrate the suture within the second channel 136 to a compressed position between the barbs 116 and the bone hole wall. In some embodiments, the suture within the first channel 132 also is compressed between the barbs 116 and the bone hole wall. A beveled surface 140 extending along the edges of the first and second channels 132, 136 and the helicity of the first and second channels 132, 136 cooperate to gradually compress the suture between the barbs 116 and the bone hole wall during rotation of the suture anchor 100.

As described hereinabove, the proximal aspect 112 is configured to receive a suitable instrument for implanting the suture anchor 100 into the bone hole. In the embodiment shown in FIG. 3, the proximal aspect 112 includes a shaped opening 144 configured to engagedly receive an instrument capable of rotating the suture anchor 100 as described above. Although in the illustrated embodiment, the shaped opening 144 is comprised of a hexalobe shape, any of various multi-lobe shapes, as well as other polygonal shapes, are also contemplated. As will be recognized, the shaped opening 144 may be used to rotate the elongate member 104 within the bone hole so as to actuate the suture anchor 100 and fixate the suture with respect to the bone. In an embodiment, the elongate member 104 is configured to be rotated through an angle of substantially 90-degrees clockwise with respect to the proximal aspect 112.

Figure 5:
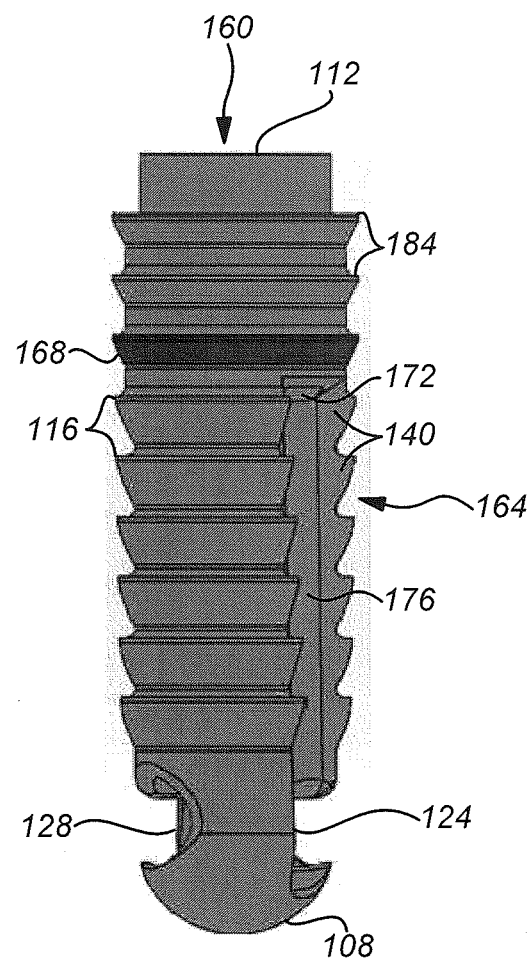
FIG. 5 illustrates a second side plan view of the suture anchor of FIG. 4.
Figure 6:
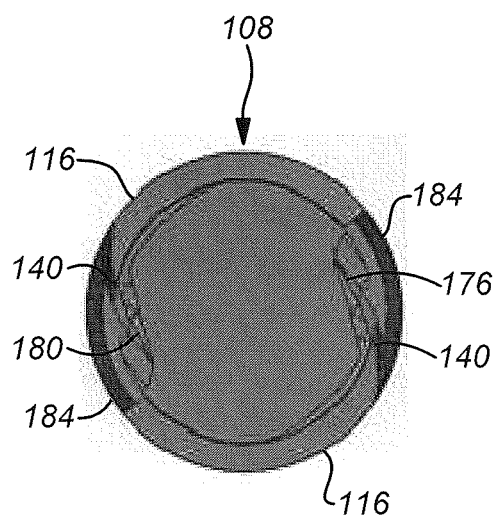
FIG. 6 illustrates a bottom plan view of a distal aspect of the suture anchor shown in FIG. 4.

FIGS. 4-6 illustrate an exemplary embodiment of a suture anchor 160 advantageously configured for fixating sutures and soft tissues to bone. The suture anchor 160 is similar the suture anchor 100, shown in FIGS. 1-3, with the exception that the suture anchor 160 includes an elongate member 164 having a depth line 168. As shown in FIGS. 4-5, the depth line 168 generally indicates proximal ends 172 of a first channel 176 and a second channel 180. It is contemplated that during operation of the suture anchor 160, the depth line 168 generally indicates a depth to which the elongate member 164 may be inserted into a bone hole while still allowing for final tensioning of a suture that is looped through a distal eyelet 120 and extending proximally within the first and second channels 176, 180.

Upon comparing the suture anchor 160 of FIGS. 4-6 with the suture anchor 100, shown in FIGS. 1-3, it will be recognized that the channels 176, 180 generally are shorter with respect to the elongate member 164 than are the channels 132, 136 with respect to the elongate member 104. As such, the suture anchor 160 includes several circular barbs 184 disposed proximal of the proximal ends 172. Unlike the barbs 116, disposed between the channels 176, 180, the circular barbs 184 extend continuously around the perimeter of the elongate member 164.

It is contemplated that the circular barbs 184 are advantageously configured to fixate the suture between the elongate member 164 and the interior wall of the drill bone hole. During operation of the suture anchor 160, a length of suture may be looped through the eyelet 120 and the elongate member 164 then inserted into a drilled bone hole with the suture laying along the first and second channels 176, 180. The elongate member 164 may be inserted into the bone hole until the depth line 168 is flush with the cortical surface of the bone. As disclosed hereinabove, the depth line 168 indicates the depth to which the elongate member 164 may be inserted into the bone hole while still allowing for tensioning of the suture extending proximally within the first and second channels 176, 180. Once the suture is desirably tensioned, the suture anchor 160 may be fully inserted into the bone hole until the proximal aspect 112 is below the cortical surface of the bone. As will be appreciated, compression of the suture between the circular barbs 184 and the interior wall of the bone hole fixates the suture with respect to the bone.

Moreover, in addition to the operation of the circular barbs 184, the suture anchor 160 is configured to be rotated through a predefined angle to compress the suture between the barbs 116 and the bone hole wall. In some embodiments, the suture within either or both of the first and second channels 176, 180 migrates between the barbs 116 and the bone hole wall when the suture anchor 160 is rotated. A beveled surface 140 extending along the edges of the first and second channels 176, 180 and helicity of the first and second channels 176, 180 cooperate to gradually compress the suture between the barbs 116 and the wall of the bone hole during rotation of the suture anchor 160. In an embodiment, the suture anchor 160 is configured to optimally capture the suture between the barbs 116 and the bone hole wall upon being rotated through an angle of substantially 90-degrees clockwise with respect to the proximal aspect 112.

Once the suture anchor 160 is suitably inserted below the cortical surface of the bone, the suture anchor 160 may be rotated within the bone hole by way of a suitable instrument that is engaged with the proximal aspect 112, as described hereinabove. For example, in some embodiments, the proximal aspect 112 may include a shaped opening, such as the shaped opening 144, that is configured to engagedly receive an instrument capable of rotating the suture anchor 160. Although in some embodiments, the shaped opening 144 is comprised of a hexalobe shape, any of various multi-lobe shapes, as well as other polygonal shapes, are contemplated. As will be appreciated, the shaped opening 144 may be used to rotate the elongate member 164 within the bone hole so as to optimally capture the suture between the barbs 116 and the interior wall of the bone hole, as described hereinabove.

In some embodiments, methods for a suture anchor, such as either of the suture anchors 100, 160, include forming an elongate member (e.g., either of the elongate members 104, 164) comprising a suitable thermoplastic polymer material, arranging a plurality of barbs 116 along the length of the elongate member, disposing an eyelet 120 in a distal aspect 108 of the elongate member, configuring the eyelet 120 to receive a suture, extending a first channel 132 and a second channel 136 along opposite sides of the elongate member, and shaping a proximal aspect 112 of the elongate member to receive an instrument for implanting the suture anchor into the bone hole.

In some embodiments, methods for a suture anchor (e.g., either of the suture anchors 100, 160) include disposing an eyelet 120 in a distal aspect 108 of an elongate member, such as either of the elongate members 104, 164, and configuring the eyelet 120 to receive a suture. In some embodiments, configuring the eyelet 120 includes orienting a first opening 124 of the eyelet 120 with respect to the first channel 132 so as to enable dynamic tensioning of the suture after the suture anchor has been inserted into the bone hole. Configuring the eyelet 120 further includes, in some embodiments, configuring a second opening 128 of the eyelet 120 to enable placing the suture into a final position with respect to the plurality of barbs 116 after implantation of the suture anchor into the bone hole.

In some embodiments, methods for a suture anchor (e.g., either of the suture anchors 100, 160) include shaping a proximal aspect 112 of an elongate member (e.g., either of the elongate members 104, 164) to receive an instrument for implanting the suture anchor into a drilled bone hole. Further, in some embodiments, shaping includes disposing a depth line 168 on the elongate member to indicate a proximal end 172 of a first channel 176 and a second channel 180, such that the depth line 168 indicates a depth within the bone hole to which the elongate member may be inserted that allows for final tensioning of the suture.

In some embodiments, methods for a suture anchor, such as either of the suture anchors 100, 160, include extending a first channel 132 and a second channel 136 along opposite sides of an elongate member, such as either of the elongate members 104, 164. Extending the first channel 132 and the second channel 136 includes, in some embodiments, helically disposing one or more of the first and second channels 132, 136 along the elongate member, such that the suture becomes gradually compressed between the plurality of barbs 116 and the bone hole during rotation of the elongate member within the bone hole. In some embodiments, arranging includes configuring the plurality of barbs 116 to cooperate with the eyelet 120 to cause the suture to remain engaged with the plurality of barbs 116 after rotation of the elongate member. In some embodiments, arranging further includes configuring the plurality of barbs 116 to engage with the wall of the bone hole upon turning of the suture anchor through a predetermined angle.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A suture anchor comprising:
    an elongate member configured to be inserted into a bone hole;
    a plurality of barbs disposed along the length of the elongate member, configured to engage with an inner wall of the bone hole, the plurality of barbs comprising at least one circular barb that extends continuously around a perimeter of the elongate member;
    an eyelet disposed in a distal aspect of the elongate member and configured to receive a suture;
    a first channel and a second channel extending along opposite sides of the elongate member;
    a beveled surface extending along the edges of the first and second channels and a helicity of the first and second channels cooperate to compress the suture during rotation of the suture anchor; and
    a proximal aspect of the elongate member configured to receive an instrument for implanting the suture anchor into the bone hole,
    wherein the proximal aspect comprises a shaped opening comprising a multi-lobe shape configured to rotate the elongate member within the bone hole.

2. The suture anchor of claim 1, wherein the elongate member is comprised of a thermoplastic polymer material.

3. The suture anchor of claim 1, wherein the eyelet is configured to receive the suture passed therethrough by way of a suture passer.

4. The suture anchor of claim 1, wherein the eyelet includes a first opening and a second opening disposed on opposite sides of the distal aspect.

5. The suture anchor of claim 4, wherein the first opening is oriented with respect to the first channel so as to enable applying tension to the suture after the suture anchor has been inserted into the bone hole.

6. The suture anchor of claim 4, wherein the second opening is configured to enable placing the suture into a final position with respect to the plurality of barbs after implantation of the suture anchor into the bone hole.

7. The suture anchor of claim 6, wherein the second opening is proximal of the first opening and canted to facilitate the final position of the suture.

8. The suture anchor of claim 1, wherein the first channel and the second channel are disposed with respect to the eyelet so as to enable applying tension to the suture after the suture anchor has been inserted into the bone hole.

9. The suture anchor of claim 8, wherein one or more of the first channel and the second channel are helically disposed along the elongate member so as to graduate compression of the suture between the plurality of barbs and an inner wall of the bone hole during rotation of the elongate member within the bone hole.

10. The suture anchor of claim 9, wherein the eyelet and the plurality of barbs cooperate to cause the suture to remain compressed between the plurality of barbs and the bone hole after rotation of the elongate member.

11. The suture anchor of claim 9, wherein the plurality of barbs are configured to engage with an inner wall of the bone hole upon turning of the suture anchor through a predetermined angle.

12. The suture anchor of claim 11, wherein the predetermined angle comprises an angle of substantially 90-degrees clockwise with respect to the proximal aspect.

13. The suture anchor of claim 1, wherein a depth line is disposed on the elongate member to indicate a proximal end of the first channel and the second channel.

14. The suture anchor of claim 13, wherein the depth line indicates a depth within the bone hole to which the elongate member may be inserted that allows for final tensioning of the suture.

15. A method for a suture anchor, comprising:
    forming an elongate member comprising a thermoplastic polymer material;

arranging a plurality of barbs along a length of the elongate member, the plurality of barbs comprising at least one circular barb that extends continuously around a perimeter of the elongate member;

disposing an eyelet in a distal aspect of the elongate member;

configuring the eyelet to receive a suture;

extending a first channel and a second channel along opposite sides of the elongate member, wherein:
 a beveled surface extends along edges of the first and second channels; and
 a helicity of the first and second channels cooperate to compress the suture during rotation of the suture anchor; and shaping a proximal aspect of the elongate member to receive an instrument for implanting the suture anchor into the bone hole, wherein the proximal aspect comprises a shaped opening comprising a multi-lobe shape configured to rotate the elongate member within the bone hole.

16. The method of claim 15, wherein configuring the eyelet includes orienting a first opening of the eyelet with respect to the first channel so as to enable applying tension to the suture after the suture anchor has been inserted into the bone hole.

17. The method of claim 15, wherein configuring the eyelet includes configuring a second opening of the eyelet to enable placing the suture into a final position with respect to the plurality of barbs after implantation of the suture anchor into the bone hole.

18. The method of claim 15, wherein extending the first channel and the second channel includes helically disposing one or more of the first and second channels along the elongate member, such that the suture becomes gradually compressed between the plurality of barbs and the bone hole during rotation of the elongate member within the bone hole.

19. The method of claim 18, wherein arranging includes configuring the plurality of barbs to cooperate with the eyelet to cause the suture to remain compressed between the plurality of barbs and the bone hole after rotation of the elongate member.

20. The method of claim 19, wherein arranging further includes configuring the plurality of barbs to engage with a wall of the bone hole upon turning of the suture anchor through a predetermined angle.

21. The method of claim 15, wherein shaping includes disposing a depth line on the elongate member to indicate a proximal end of the first channel and the second channel, such that the depth line indicates a depth within the bone hole to which the elongate member may be inserted that allows for final tensioning of the suture.

* * * * *